United States Patent [19]

Wirz

[11] Patent Number: 4,669,873
[45] Date of Patent: Jun. 2, 1987

[54] SPECTROPHOTOMETER

[75] Inventor: Peter Wirz, Waldernbach, Fed. Rep. of Germany

[73] Assignee: Leybold-Heraeus GmbH, Cologne, Fed. Rep. of Germany

[21] Appl. No.: 703,926

[22] Filed: Feb. 21, 1985

[30] Foreign Application Priority Data

Feb. 24, 1984 [DE] Fed. Rep. of Germany ....... 3406645

[51] Int. Cl.$^4$ ............................ G01J 3/42; G01J 3/46; G01N 21/01
[52] U.S. Cl. ...................................... 356/73; 356/328
[58] Field of Search ................... 356/72, 73, 326, 328, 356/382, 402, 432, 436; 250/227

[56] References Cited

U.S. PATENT DOCUMENTS 4,566,792  1/1986  Suzuki ............................... 356/328

FOREIGN PATENT DOCUMENTS 0119822   9/1981   Japan ................................. 356/328
0168145  12/1981   Japan ................................. 356/432
0073632   5/1982   Japan ................................. 356/73.1
0131007   8/1982   Japan ................................. 356/382
2064113   6/1981   United Kingdom ................. 356/402

OTHER PUBLICATIONS

Prince et al. "Apparatus for Simultaneous Measurements of Mass Change, Optical Transmittance, and Reflectance of Thin Films" J. Vac. Sci. Technol., 16(2) (Mar./Apr. 1979), pp. 244–247.

Primary Examiner—Vincent P. McGraw
Attorney, Agent, or Firm—Felfe & Lynch

[57] ABSTRACT

A spectrophotometer obtains transmitted, reflected, or radiated light from at least two measuring points on at least one object and a spectroscopic light disperser disperses the obtained light spectroscopically to measuring cells for electrically indicating the spectrum of the obtained light, whereby the spectrum may be analyzed for indicating optical properties of the object at the measuring point from which the light was obtained. At least one fibre-glass cable respectively carries the light obtained at each measuring point to the spectroscopic light disperser. The ends of the fibres of each cable at the spectroscopic light dispersion are arranged in a row and the row of fibre ends of each cable are parallel to each other in a matrix of fibre ends. At least one light stop allows light from only one fibre-glass cable at a time to carry the light to the spectroscopic light disperser.

12 Claims, 7 Drawing Figures

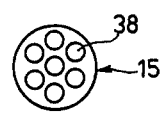
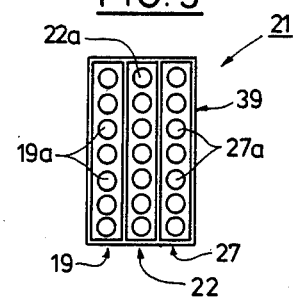
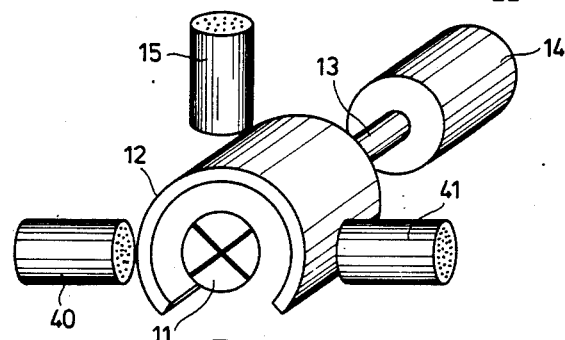
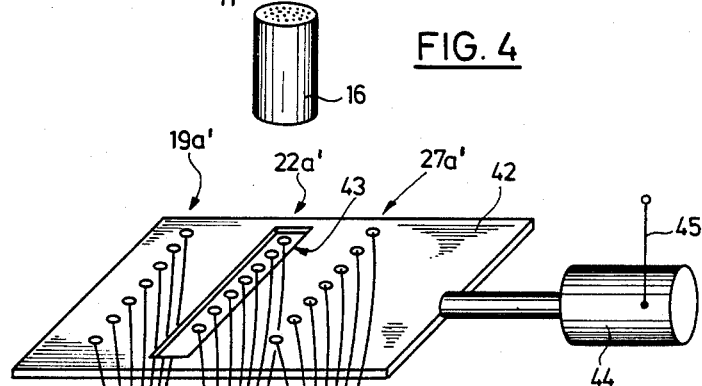
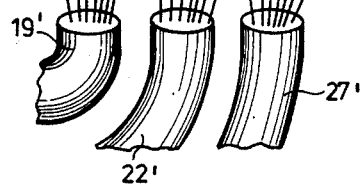

SPECTROPHOTOMETER

A spectrophotometer measures the optical properties of a light-transparent, -reflecting and/or -radiating material in dependence upon the light wavelengths therefrom. It is particularly useful for measuring the change in optical properties during the production of a thin layer on a substrate in a vacuum chamber. In one arrangement for this, at least one optic fibre (hereinafter called fibre-glass) carries light at least part of the way from the layer to a spectroscopic light disperser. A series of measuring cells receive respective spectrographically-separated portions of the light from the disperser and an electrical analyzer cyclically interrogates the measuring cells to provide a spectral analysis of the light from the layer and, thereby, an analysis of the optical properties of the layer.

In the manufacture and/or quality control of optical products such as filters, mirrors and lenses, it is often necessary to measure the optical properties in dependence upon the light wavelengths and to represent the "spectrum" graphically, i.e. to process it by computer methods. Typical of this are dereflection layers, particularly for wide-band dereflection, which are required to give the smallest possible reflection within the range of visible light. Such layers generally consist of a large number of individual layers having differing refractive indices, (interference layer systems, as they are called). During production, the build-up, with time, of each individual layer has to be monitored; the end product has to be examined to ensure that it falls within the permitted tolerance range. A further example is that of filter layers, e.g. infrared filters, which hold back heat radiation, but are intended to allow visible light to pass through with the least possible hindrance. Yet another example is that of what are called cold light mirrors, which reflect the shortwave "cold" light beam into an optical system, but permit troublesome heat radiation of greater wavelength to pass or without restriction (e.g., projector lamps).

In the production of layers or layer systems of this kind as well as in final control, it is necessary to carry out a measurement of the spectrum dependence of the properties of the coatings. During production of the coatings, the measured values can also be used for controlling the production process, for example, for regulating the rate of deposition of the layer material or for finally switching off the coating process after completion of a layer or of the entire layer system. The literature contains numerous proposals relating to photometer arrangements for measuring the spectrum dependence of the properties of the coatings.

The paper entitled "A thin film monitor using fibre optics" by H. M. Runciman, W. B. Allan and J. M. Ballantine, and published in J. Sci. Instrum. 1966, vol. 43, pages 812 to 815, discloses the idea of passing measuring light from a light source through a first fibre-glass cable into a vacuum chamber and into the direct vicinity of the measuring object and of passing the reflected measuring light, through a second fibre-glass cable, out of the vacuum chamber and to a detector and an analyzing means. In this arrangement a complete measuring system is required for each measuring point for each measuring object.

U.S. Pat. No. 3,874,799 discloses a spectrophotometer wherein the light emerging from the measuring object is dispersed into a spectrum by a light-dispersion means designed as a diffraction screen, and is passed to a photo-receiver means, which takes the form of individual photo-diodes arranged in a row. Because of their spatial location, each of these diodes, arranged extremely closely to each other, is associated with a very specific wavelength, so that the change in intensity of the spectrum in dependence upon the wavelengths can be determined by cyclic interrogation of the diodes. Here again, a separate measuring and analyzing means is necessary for each individual measuring point.

Germany Patent No. 16 55 272 discloses a spectrophotometer arrangement of the initially described kind, the light-dispersion means of which corresponds to a large extent to that described in U.S. Pat. No. 3,874,799. Also present is a light conductor constituted by a fibreglass cable which passes the measuring light from a vacuum chamber to the inlet gap in a light-dispersion means which also contains a concave diffraction screen. In this case too, a separate measuring arrangement is required for each measuring point.

A further field of application is that of monitoring beam-emitiing material in vacuum-coating processes. Thus, for example, it may be necessary to monitor and/or regulate thermal vapour-depositing sources which give off thermal radiation, or plasma processes which are accompanied by light phenomena, such as for example cathodic atomization methods.

To meet the need for achieving increasingly more accurate process control by means of more measuring points, a considerable number of measuring and analyzing systems have been required when applying the known measuring principles. The object of the present invention is, therefore, to enable a larger number of mutually independent measuring points or measuring objects to be covered by a single measuring and analyzing system while maintaining measuring accuracy.

To this and other ends, the invention is used in a spectrophotometer providing light transmitted, reflected, or radiated from two or more measuring points on one or more objects. At least one optic fibre or fibreglass respectively carries the light from each measuring point to a spectroscopic light disperser which spectroscopically disperses the light from each optic fibre onto measuring cells, for example, photodiodes, for electrically indicating the light spectrum and, thereby, analyzing the optical properties at the measuring points of the object transmitting, reflecting or radiating the light.

In order to associate the analysis with one of the measuring points at a time, a light stop or shutter is arranged to block the transmitted, reflected, or radiated light from all but one of the optic fibres respectively associated with the measuring points. Light from only one measuring point at a time is then carried over the respective optic fibre to the spectroscopic light disperser for analysis. With transmitted and reflected light, at least, this can be done with a light stop operative on the source of light for the transmittance or reflectance from the measuring point. In all cases, however, it can be done with a light stop operative on the optic fibres from the measuring points to the spectroscopic light disperser.

The ends of the optic fibres at the spectroscopic light disperser generally are not coincident. As a result, the spectrum of the light from the respective fibres on the measuring cells does not frequency correlate for the respective measuring cells. That is, the frequency (wavelength) of light spectroscopically dispersed to the respective measuring cells is different in dependence on the optic fibre providing the light. Electronic calibration can compensate for this.

Several optic fibres (a fibre-glass cable) are preferred for carrying the light from each measuring point to the spectroscopic light disperser to carry more light and for other reasons. The ends of the optic fibres of the respective cables at the spectroscopic light disperser are then non-coincident. It is then preferred to arrange the ends of the optic fibres of each cable in a row and to arrange the rows of fibre ends from each cable in parallel to form a matrix of fibre ends. The row arrangement provides narrow, strip-like light entry to the disperser which improves its resolution and admits of a further-preferred, even-narrower slot mask along the row for still further resolution improvement as well as other advantages. The matrix of fiber-end rows fixes the spectrum shift on the measuring cells from the different row locations on the spectroscopic light disperser for fixed precision and other advantages.

The preferred embodiment is, therefore, at least one fibre-glass cable associated with each measuring point, ends of the fibers of each fiber-glass cable that run into the spectroscopic light disperser being, in each case, arranged in a row. The rows of the fiber ends of all the fiber-glass cables are arranged in parallel and immediately adjacent each other in a fibre-glass matrix. At least one light stop is associated with the fibre-glass cables for selecting an individually-operative beam path from a measuring point.

The row/matrix arrangement of fibre-glass cables at the spectroscopic light disperser and the associated light stop control, as proposed in the invention, enable a single spectroscopic light disperser and analyzing circuit downstream thereof to accommodate a corresponding number of measuring points or measuring objects. In this way, the expense involved is reduced to a corresponding fraction of that otherwise incurred. In addition, further measuring points are accommodated by an additional row of fibers at the input of the spectroscopic light disperser.

Because the differing position of the slots or rows of fibers causes displacement of the wavelength correlation of the spectrum, it is necessary to compensate for this. This can be readily achieved by, for example, comparison with a known line spectrum and a computation in a microprocessor associated with the analyzing means. It is also possible to interrogate the individual measuring points rapidly one after the other in a cyclic sequence and to correlate the results of analysis with the individual measuring points. The necessary synchronization can also be achieved by the microprocessor. Experience has shown that the time for covering a spectrum is approximately 50 milliseconds and the time for processing the measured values is generally longer. The system therefore can be switched to another measuring point during the processing time. It is also possible, using the same system, to carry out analysis on gas atmospheres in the processing chamber.

Merely-illustrative preferred embodiments and their modes of operation and advantages are set forth in the following detailed description with reference to the accompanying drawings, in which:

FIG. 2 is an end cross-sectional view on line II—II of a portion of the embodiment shown in FIG. 1;

FIG. 3 is a bottom view along line III—III of another portion of the embodiment shown in FIG. 1;

FIG. 4 is a perspective view of still another portion of the embodiment shown in FIG. 1;

FIG. 5 is a perspective view of an alternative embodiment of the portions shown in FIGS. 3 and 4;

Figure 1:
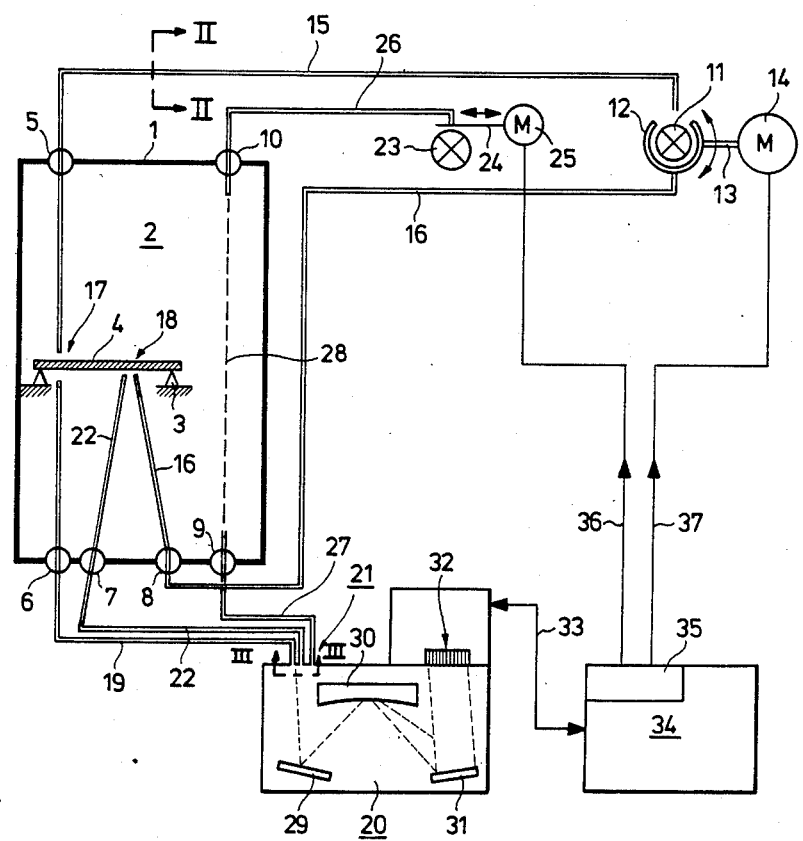
FIG. 1 is a schematic of one preferred embodiment.

Illustrated in FIG. 1 is a vacuum chamber 1 which, however, could be replaced by any other reaction chamber required. The vacuum chamber encloses a process compartment 2 in which a known coating process, such as vacuum vapour deposition, cathodic atomization, chemical vapour deposition (CVD) etc., can be carried out. The apparatus required for these coating processes is also known and, therefore, omitted from the drawings for the sake of simplicity. In the process compartment 2 is an object holder 3 (shown only diagrammatically) on which rests an object to be measured (herein called a measuring object) 4. It may be a single continuous substrate for the coating process, but also may consist of a plurality of individual substrates which are coated simultaneously. The vacuum chamber 1 comprises a series of vacuum passages 5 to 10 of known construction, so that further details thereof are unnecessary. The measuring object 4 is that part, the transmission and reflection properties of which are to be continuously examined in dependence upon the wavelength.

For this purpose, a light source 11, which emits a continuous beam and is surrounded by a rotatable light stop 12, is located outside the vacuum chamber. The light stop 12 is connected to a servo-motor 14 by way of an adjusting shaft 13, so that the light from the light source 11 can be optionally emitted in a predetermined direction, whereas all other directions are screened off. Details of this light stop system will be described in greater detail by reference to FIG. 4.

Fibre-glass cables 15 and 16 pass from the light source 11 through the vacuum passages 5 and 8 respectively into the vacuum chamber 1 and into the immediate vicinity of the measuring object 4. The location of the ends of the fibre-glass cables 15 and 16 define measuring points 17 and 18 respectively, which relate to locally limited points of the measuring object 4 or to individual substrates when the measuring object 4 consists of a plurality of individual substrates.

The light which enters at the measuring point 17 (iransmission measurement) is passed through a fibre-glass cable 19. which extends through the vacuum passage 6, to a light-dispersion means 20 such as is described for example, in U.S. Pat. No. 3,874,799 and in German Patent No. 26 25 272. Located at the entry point 21 is a row of parallel slots which will be described in detail in connection with FIG. 3. It will be understood that the ends of the fibre-glass cables 15 and 19 which are disposed in the immediate vicinity of the measuring object 4 are in alignment with each other.

Not only is the inner end of the fibre-glass cable 16 directed on to the measuring point 18, but also, from the same side, the inner end of a fibre-glass cable 22. What is known as a reflection measurement is carried out in the stated manner in the zone of the measuring point 18. The fibre-glass cable 22 passes through the vacuum passage 7 to a further slot in the zone of the inlet point 21 of the light-dispersion means 20.

It will be understood that optical systems, which to a large extent cut out light losses, can be provided at the inner ends of the fibre-glass cables 15, 16, 19 and 22.

Arranged outside the vaccum chamber 1 is a further light source 23 which is designed as a line emitter. Associated with this light source is a further light stop 24 which is actuated by a servo-motor 25. The light from the monochromatic light source 23 is passed into the process compartment 2 by way of a fibre-glass cable 26 and the vacuum passage 10, and the fibre-glass cable 26 of course terminates just to the rear of the vacuum passage 10. Located at a precisely opposite point of the vacuum chamber 1—and in an aligned position—is a further fibre-glass cable 27 which is secured in the vacuum passage 9. Here again, the two ends of the fibre-glass cables that are directed on to each other can be provided with suitable optical means for bunching the light. Located between the ends is a further measuring point 28, which is formed by the open beam path between the ends of the fibre-glass cables 26 and 27. In this way the spectrum of the gas atmosphere in the process compartment 2 can be covered. The fibre-glass cable 27 is also passed to a slot located at the entry point 21.

In the known manner, the light-dispersion means 20 incorporates a deflecting mirror 29, a diffraction screen 30 (convex mirror with lattice structure) and a further deflecting mirror 31. The spectrally dispersed light, reflected by the deflecting mirror 31, strikes a photo-receiver means 32 which, likewise in known manner, takes the form of an array of diodes. The actuation and measuring signals are transmitted through a multiple cable 33 to a computer unit 34, in which the mathematical analysis and/or indication of the measuring signals in spectrum distribution is carried out. The computer unit 34 also contains a control unit 35, by means of which the servo motors 25 and 14 are controlled through two control lines 36 and 37 respectively in the manner described in more detail below.

FIG. 2 shows a greatly simplified cross-section through a known fibre-glass cable 15; the number of individual fibres is greatly reduced in the drawing, but their diameter is greatly exaggerated. A fibre-glass cable for the above-mentioned purposes normally comprises several dozen individual fibres having a diameter of 200 μm and 100 μm in the minimum case. In the present case only seven individual fibres in all are illustrated.

As shown in FIG. 3, the fibres 38 are in each case arranged in a closed row at the ends at which they enter the light-dispersion means 20 (FIG. 1); FIG. 3 in fact shows the fibres, arranged in a row, of three fibre-glass cables, in the present case therefore, of the fibre-glass cables 19, 22 and 27 shown in FIG. 1. The rows 19a, 22a and 27a concerned extend immediately adjacent and parallel to each other and together form a fibre-glass matrix 39. This fibre-glass matrix is so arranged at the entry point 21 of the light-dispersion means 20 that the ends of the individual fibres are directed on to the deflecting mirror 29. In the manner described in greater detail hereinafter, care is taken to ensure that, during the measurement, only one of the rows of fibres is always covered and analyzed. It is important that the longitudinal axes of the rows 19a, 22a and 27a be directed at right angles to the diffraction direction and at right angles to the serial arrangement of the photo-receivers.

FIG. 4 shows details in the zone of the light stop 12 in FIG. 1. The light stop consists of a 270-degree sector of a hollow cylinder, which is arranged concentrically around the light source 11 and can be rotated about its axis by means of the adjusting shaft 13 and servo motor 14. The ends of four fibre-glass cables are arranged equidistantly around the light source 11, the ends of the fibre-glass cables 15 and 16 being located at the top and bottom respectively. Arranged at the left and right are the ends of two further fibre-glass cables 40 and 41 respectively, by means of which measuring lines can be applied to two further measuring points. The measuring points concerned are not, however, illustrated in FIG. 1, so as not to overload the drawing. Depending upon the angular position of the light stop 12, measuring light is applied only to one of these fibre-glass cables. In the present case, the light stop 12 has been rotated through 180 degrees from its FIG. 1 position, so that measuring light is applied only to the fibre-glass cable 16 for the measuring point 18; the other fibre-glass cables are screened off. In this way, measuring light can be applied as required to any selected fibre-glass cable; in FIG. 1 the fibre-glass cable 15 is receiving measuring light.

The equipment described operates in the following manner:

In the position of the light stops 12 and 24 as illustrated in FIG. 1, measuring light is applied only to the fibre-glass cable 15 for the purpose of carrying out a transmission measurement at the measuring point 17. The part of the measuring light that passes through emerges at the end of the fibre-glass cable 19 from the glass fibres which are there arranged in a row 19a (FIG. 3). Darkness obtains at the ends of the fibres in the rows 22a and 27a.

If a reflection measurement is to be carried out at the measuring point 18, the control unit 35 switches the light stop 12 into the opposite position, shown in FIG. 4, by way of the control line 37 and the servo-motor 14. The measuring light then enters the fibre-glass cable 16, and the reflected portion thereof passes through the fibre-glass cable 22 to the inlet point 21 into which the arrangement of rows 22a here present discharges. The light beams emerging here are then subjected to spectrum dispersion in the light-dispersion means 20 and are analyzed by means of the photo-receiver means 32. During this measurement, darkness obtains at the ends of the fibres in the zone of the rows 19a and 27a.

On commencement of the measurement, what is known as an underground spectrum $I_O$ is retrieved and this is then compared with the spectrum I occurring in the process. By means of a quotient formation $I/I_O$ a spectrum which is for example independent of the lamp spectrum and of the transmission properties of the glass fibres, is thus obtained. If the line spectrum is then to be covered, the light stop 12 is rotated through 90 degrees by means of the control unit 35, so that measuring light is not applied to the two fibreglass cables 15 and 16. At the same time the control unit 35 actuates the servo-motor 25 by way of the control line 36 in such manner that the light stop 24 allows light to enter the fibre-glass cable 26. The portion of the light beam that passes through the process compartment is then applied, through the fibre-glass cable 27, to the arrangement of rows 27a in the zone of the entry point 21 (FIG. 3), whereas darkness obtains at the rows 19a and 22a. Thus, in this case, the spectrum characteristics of the gas atmosphere in the process compartment 2 are covered by means of the photo-receiver unit 32.

By means of the arrangement of rows shown in FIG. 3, each fibre-glass cable is spread out within a narrow slot, the widih corresponding approximately to the thickness of a single fibre and being determinative as regards the spectrum resolution of the analyzing means.

The combination forming the matrix 39 enables the individual slots or lines to be accommodated in a very narrow space. Switching from one row to another corresponds to a displacement at the input of the light-dispersion means 20. This also stipulates a displacement of the spectrum on the photo-receiver unit 32. By means of a wavelength calibration of the various measuring cells of the photo-receiver unit 32 by means of a beam emitter having specific lines, the corresponding wave calibration is correlated with the spectrum from the measuring point concerned by way of the computer unit.

The light stops 12 and 24 do not need to be arranged at the side of the fibre-glass cables 15, 16 and 26 as shown in FIG. 1. It is also possible for a light stop 42, which can be arranged within the light-dispersion means 20 and which comprises a lot 43, to be associated with the inlet point 21. A variant of this kind is illustrated in the reverse position in FIG. 5. The individual rows 19a, 22a and 27a of the ends of the various glass fibres are arranged in the matrix 39, illustrated in FIG. 3, and the slot 43 in the light stop 42 is movable as required relatively to each row 19a, 22a and 27a so that in each case only a single row is uncovered for analyzing the brilliancy distribution of the spectrum. For the purpose of actuating the light stop 42, a further servo-motor 44 is provided and this can be switched to the control unit 35 through a control line 45. As shown in FIG. 5, an additional light stop 42 can be provided so as to prevent any scattered light that might be present from entering the light dispersion means 20. In such a case, control of the light stops 12 and 24 must of course be co-ordinated.

The distance between the rows is exaggerated in the drawings. It is recommended that the distance should be as small as possible and that the slot should be as narrow as possible. If, for example, the width of the slot is less than the diameter of the individual glass fibres, this can improve the optical resolving properties of the entire system.

Figure 6:
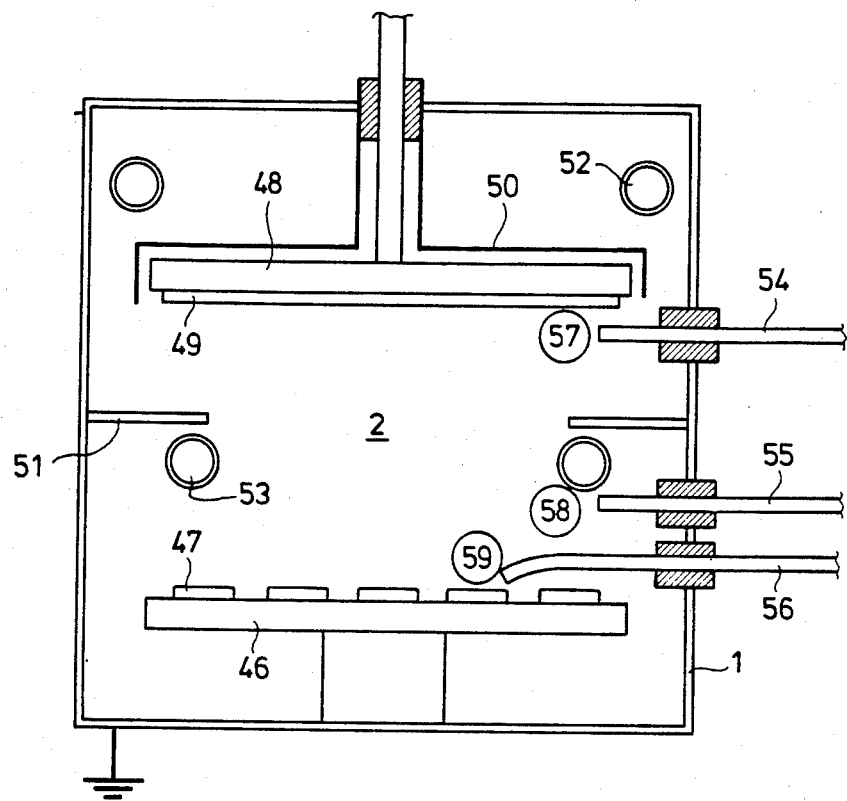
FIG. 6 is a schematic of a portion of another preferred embodiment.

FIG. 6 likewise illustrates a vacuum chamber 1 which encloses a process compartment 2. This accommodates a substrate holder 46 carrying a row of disc-shaped substrates 47. Disposed opposite the substrate holder is a planar parallel arrangement comprising a cathode 48 with a target 49 made of the material to be atomized. The cathode 48 is surrounded by an earthing screen 50.

Part of the process compartment 2 is divided by a light stop 51. At one side of the light stop is an annular distributing line 52 for the supply of the atomization gas (argon), and at the other side of the light stop is located an annular distributing line 53 for supplying a reaction gas. These lines are indicated only by their cross-sectional faces, and for the sake of simplicity, the connecting lines leading from the vacuum chamber 1 have been omitted from the drawing.

A fibre-glass cable 54 runs into the process compartment 2 in the zone of the target 49. During operation of the equipment, a luminous plasma is present near the target, so that by means of the fibre-glass cable 54 it is possible to monitor the composition of the plasma and, in particular, to determine whether only the required material leaves the surface of the target, i.e. to ascertain its composition. In this case therefore, no outside light source is present, and instead the light beam from the material itself is used for the analysis.

At one side of the light stop 51, a further fibre-glass cable 55 runs into the reaction compartment 2, this cable being used for checking the composition of the admitted reaction gas when this is a gas mixture, for example. Furthermore, by means of the fibre-glass cable 55 it is also possible to arrive at conclusions regarding the coating forming on the substrates 47. For example, particles from a metallic target 49 can occur in the form of dust and these particles can become oxidized on their way to the substrates. By means of the fibre-glass cable 55 it is possible, for example, to examine the relative degree of oxidation of the atomized particles.

Finally, a further fibre-glass cable 56 runs into the process chamber 2 in the direct vicinity of the substrate 47. With this arrangement it is possible to monitor an etching process, for example. If, during the etching, a coating is penetrated, then material of the subjacent coating passes into the reaction chamber. The material is excited and emits a characteristic beam which can serve as an indication that the process concerned can be terminated.

The ends of the fibre-glass cables, which can likewise be provided with optical means at this point, define measuring points 57, 58 and 59, the position of which is not fixed within such narrow limits as are indicated in FIG. 6.

The fibre-glass cables 54, 55 and 56 are in this instance also passed to a fibre-glass matrix as illustrated in FIG. 3, i.e. the ends of the glass-fibres are broadened in each row. Control of the individual rows of fibres can be carried out in the same way as that illustrated in FIG. 5, i.e. a light stop 42 comprising a slot can be brought into association with each row of fibres by translatory movement.

Figure 7:
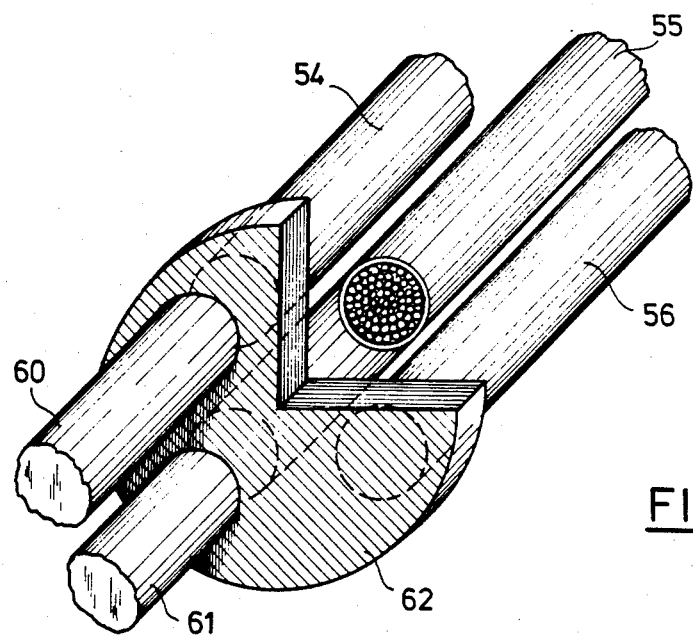
FIG. 7 is a perspective view of an alternative embodiment to that of FIG. 4.

The beam paths can be interrupted at various points along the fibre-glass cable. FIG. 7 illustrates part of such a variant. The ends of the fibre-glass cables 54 to 56 that are disposed outside the process compartment 2 are equidistantly distributed on a circle, as illustrated in FIG. 7 - the fourth fibre-glass cable that is shown is used simply for storage purposes. Aligned with the fibre-glass cables is a corresponding number of similar fibre-glass cables, of which only the cables 60 and 61 are illustrated in FIG. 7. These lead to a fibre-glass matrix 39 as illustrated in FIG. 3. The mutually aligned ends of all of the fibre-glass cables are spaced from each other, and a light stop 62 is arranged in the space; this light stop is mounted on the shaft of a servo-motor, not illustrated, but as shown in FIG. 4. The light stop is what is known as a sector light stop in which the dimensions of the cut-away sector portion are such that only a beam path of two aligned fibre-glass cables (e.g. 54 and 60) are uncovered, whereas the beam paths of the other fibre-glass cables are interrupted. Also, use can be made of a further form and position of the light stop such that all of the light conductors are switched off in one position in order to determine a dark spectrum of the detector.

Interrogation of the various measuring points can be carried out cyclically and at a relatively high frequency when this system is used so that a multiplex operation is possible. In this way all of the measuring points can be observed on an almost continuous basis. The term "light stop" will be understood as meaning any device for interrupting the beam paths, for example a device for producing a polarization effect in the fibre-glass cables in conjunction with polarization filters.

It will be understood that the specification and examples are illustrative but not limitative of the present invention and that other embodiments within the spirit and scope of the invention will suggest themselves to those skilled in the art.

What is claimed is:

1. In a spectrophotometer having means for obtaining transmitted, reflected, or radiated light from at least two measuring points on at least one object, the improvement comprising:

a spectroscopic light dispersion means for dispersing obtained light spectroscopically;

a photo-receiver unit having measuring cells for electrically indicating the spectrum of the obtained, dispersed light;

at least two fibre-glass cables for respectively carrying light obtained at least at two measuring points to the spectroscopic light dispersion means as the obtained light, ends of the fibres of each cable at the spectroscopic light dispersion means being arranged in a row and the row of fibre ends of each cable being parallel to each other in a matrix of fibre ends;

at least one light stop means for allowing only one fibre-glass cable at a time to provide the obtained light to the spectroscopic light dispersion means; and means for electronically correlating the measuring cells of the photo-receiver unit with each row of the ends of the fibres in the matrix;

whereby the spectrum may be analyzed for indicating optical properties of the object from which the light was obtained.

2. The spectrophotometer according to claim 1, and further comprising:

a second fibre-glass cable associated respectively with each measuring point for providing the light obtained therefrom.

3. The spectrophotometer according to claim 2, wherein the light stop means comprises one light source communicating with more than one of the second fibre-glass cables and a light stop between the light source and the light-inlet ends of the second fibre-glass cables and uncovering only one of the second fibre-glass cables at a time for entry of light thereinto.

4. The spectrophotometer according to claim 2, wherein the light stop means comprises a slot movable over the fibre-end matrix for uncovering and passing light from only one row thereof at a time to the spectroscopic light dispersion means.

5. The spectrophotometer according to claim 3, and further comprising a substantially-monochromatic light source for at least one of the second fibre-glass cables.

6. The spectrophotometer according to claim 4, and further comprising a substantially-monochromatic light source for at least one of the second fibre-glass cables.

7. The spectrophotometer according to claim 1, and further comprising means responsive to the electrical indication of the spectrum by the spectroscopic light dispersion means for actuating the light stop means.

8. The spectrophotometer according to claim 2, and further comprising means responsive to the electrical indication of the spectrum by the spectroscopic light dispersion means for actuating the light stop means.

9. The spectrophotometer according to claim 3, and further comprising means responsive to the electrical indication of the spectrum by the spectroscopic light dispersion means for actuating the light stop means.

10. The spectrophotometer according to claim 4, and further comprising means responsive to the electrical indication of the spectrum by the spectroscopic light dispersion means for actuating the light stop means.

11. The spectrophotometer according to claim 5, and further comprising means responsive to the electrical indication of the spectrum by the spectroscopic light dispersion means for actuating the light stop means.

12. The spectrophotometer according to claim 6, and further comprising means responsive to the electrical indication of the spectrum by the spectroscopic light dispersion means for actuating the light stop means.

* * * * *